(12) United States Patent
Kojima

(10) Patent No.: US 6,232,288 B1
(45) Date of Patent: May 15, 2001

(54) COMPOSITION FOR IMPROVING PANCREATIC FUNCTION

(75) Inventor: Itaru Kojima, Maebashi (JP)

(73) Assignee: Takeda Chemical Industries, Ltd., Osaka (JP)

(*) Notice: Subject to any disclaimer, the term of this patent is extended or adjusted under 35 U.S.C. 154(b) by 0 days.

(21) Appl. No.: 09/051,624

(22) PCT Filed: Nov. 8, 1996

(86) PCT No.: PCT/JP96/03277

§ 371 Date: Apr. 15, 1998

§ 102(e) Date: Apr. 15, 1998

(87) PCT Pub. No.: WO97/17086

PCT Pub. Date: May 15, 1997

(30) Foreign Application Priority Data

Nov. 9, 1995 (JP) ................................................. 7-291238

(51) Int. Cl.[7] ........................................................ A01N 37/18
(52) U.S. Cl. ........................................ 514/2; 514/12; 514/8
(58) Field of Search ......................................... 514/2, 12, 8

(56) References Cited

FOREIGN PATENT DOCUMENTS 0 555 785 A1    8/1893  (EP) .

OTHER PUBLICATIONS

Bowie et al., Science 247:1306–1310, 1990.*
Ngo et al., The Protein Folding Problem and Tertiary Structure Prediciton, Merz et al., eds., Birkhauser, 1994.*
Wells, Biochemistry 29:8509–8517, 1990.*
"Betacellulin and Activin A Coordinately Convert Amylase–secreting Pancreatic AR42J Cells Into Insulin–secreting cells", The American Society for Clinical Investigation, Inc., vol. 97, No. 7, (1996), pp. 1647–1654.
"Betacellulin, a member of the epidermal growth factor family, is overexpressed in human pancreatic cancer", International Journal of Oncology 7: pp. 825–829, 1995.

* cited by examiner

*Primary Examiner*—Elizabeth Kemmerer
(74) *Attorney, Agent, or Firm*—David G. Conlin; Cara Z. Lowen; Dike, Bronstein, Roberts & Cushman

(57) ABSTRACT

The present invention provides a novel composition comprising a betacellulin protein, or a fragment thereof, which is capable of promoting the differentiation of undifferentiated pancreatic cells into insulin-producing beta cells or pancreatic polypeptide producing F cells. This composition can also improve glucose tolerance in patients and inhibit the growth of undifferentiated pancreatic cells. The composition may further comprise activin and/or other molecules. Methods for treating mammals, including humans, are also provided.

26 Claims, 7 Drawing Sheets

COMPOSITION FOR IMPROVING PANCREATIC FUNCTION

This application is a national stage application of PCT application Serial No. PCT/JP96/03277, filed Nov. 8, 1996.

TECHNICAL FIELD

The present invention relates to a composition for improving pancreatic function, a composition for promoting differentiation of undifferentiated pancreatic stem cells to pancreatic beta cells, or a composition for preventing or treating undifferentiated pancreatic cancer, which comprises a betacellulin protein or a mutein thereof.

BACKGROUND ART

A betacellulin protein (hereinafter also referred to as BTC protein) is a peptide factor produced by pancreatic beta tumor cells derived from a transgenic mouse, and its full amino acid sequence has been clarified by cDNA analysis [Shing et al., Science, 259:1604 (1993); Sasada et al., Biochemical and Biophysical Research Communications, 190:1173 (1993)]. Although BTC protein was first discovered as a factor possessing mouse 3T3 cell growth-promoting activity, it was later found to exhibit growth-promoting activity against vascular smooth muscle cells and retinal pigment epithelial cells [Shing et al., Science, 259:1604 (1993)].

A human BTC protein naturally occurs in very trace amounts, and attempts to obtain it from human tissue has been very difficult by various limitations. In recent years, however, gene engineering techniques have been successfully used to produce highly purified human BTC protein in large amounts and at relatively low costs (EP-A-0555785). Also, it has been reported that BTC protein can be used in the treatment of diseases such as wounds, tumors and vascular malformations, and preparation of competitive agents such as an antibodies or false peptides which can be used in the treatment of such diseases attributable to smooth muscle growth as atherosclerosis and diabetic retinopathy (EP-A-0482623, EP-A-0555785).

In addition, the mRNA of BTC protein has been detected in non-brain organs, e.g., liver, kidney and pancreas, suggesting that BTC protein exhibits some function in these organs as well, but much remains to be known in detail.

DISCLOSURE OF THE INVENTION

Diabetes mellitus is a disease characterized by the onset of various complications associated with persistent hyperglycemia. This disease is classified into insulin-dependent, insulin-independent and other types, and is thought to be associated with diverse causes, but basically it develops when insulin action is diminished. Insulin-dependent diabetes mellitus, in particular, is caused by an absolute lack of insulin production. Against this background is there a need for the development of a medicine which improves pancreatic function to prevent or treat diabetes mellitus etc.

In view of the above problems, the present inventors made extensive investigation and found that known BTC protein acts on cells derived from the pars exocrina pancreatis capable of multiple differentiation to allow them to differentiate to beta cells etc. The present inventors made further investigation based on this finding, and developed the present invention.

Accordingly, the present invention provides:
(1) A composition for improving pancreatic function which comprises a betacellulin protein or a mutein thereof;
(2) The composition according to (1), wherein the betacellulin protein is a protein having the amino acid sequence shown by at least one SQ ID NO. selected from the group consisting of SEQ ID NO:3, SEQ ID NO:4, SEQ ID NO:5 and SEQ ID NO:6;
(3) The composition according to (1), wherein the betacellulin protein is a protein having the amino acid sequence shown by SEQ ID NO:1 or a protein having the amino acid sequence shown by SEQ ID NO:2;
(4) The composition according to (1), wherein the mutein of the betacellulin protein is a protein having (i) an amino acid sequence resulting from deletion of about 1 to 40 amino acids from the amino acid sequence shown by SEQ ID NO:1 or SEQ ID NO:2, (ii) an amino acid sequence resulting from replacement of about 1 to 40 amino acids in the amino acid sequence shown by SEQ ID NO:1 or SEQ ID NO:2 by other amino acid sequences, or (iii) an amino acid sequence resulting from addition of about 1 to 40 amino acids to the amino acid sequence shown by SEQ ID NO:1 or SEQ NO:2;
(5) The composition according to (1), wherein the mutein of the betacellulin protein is a protein having an amino acid sequence resulting from deletion of 12 or 30 amino acids from the N-terminus of the amino acid sequence shown by SEQ ID NO:1;
(6) The composition according to (1) to (5), which further contains an activin;
(7) The composition according to (6), wherein the content ratio of the activin to the betacellulin protein or a mutein thereof is about 1:10 to 10:1;
(8) The composition according to (1) to (7), which is a composition for preventing or treating diabetes mellitus.
(9) The composition according to (1) to (7), which is a composition for preventing or treating pancreatic dysfunction in diabetes mellitus or pancreatic hypofunction associated with senile insulin secretion reduction;
(10) A composition for promoting differentiation of undifferentiated pancreatic stem cells to pancreatic beta cells, which comprises a betacellulin protein or a mutein thereof;
(11) A composition for preventing or treating undifferentiated type of pancreatic cancer, which comprises a betacellulin protein or a mutein thereof;
(12) A method for improving pancreatic function of human or mammal, which comprises administering an effective amount of a betacellulin protein or a mutein thereof to human or mammal;
(13) A method for promoting differentiation of undifferentiated pancreatic stem cells to pancreatic beta cells of human or mammal, which comprises administering an effective amount of a betacellulin protein or a mutein thereof to human or mammal;
(14) A method for preventing or treating undifferentiated type of pancreatic cancer of human or mammal, which comprises administering an effective amount of a betacellulin protein or a mutein thereof to human or mammal;
(15) A use of a betacellulin protein or a mutein thereof for the manufacture of a composition for improving pancreatic function;
(16) A use of a betacellulin protein or a mutein thereof for the manufacture of a composition for promoting differentiation of undifferentiated pancreatic stem cells to pancreatic beta cells;

(17) A use of a betacellulin protein or a mutein thereof for the manufacture of a composition for preventing or treating undifferentiated pancreatic cancer.

Also, the present invention further provides:

(18) A composition for improving pancreatic function which comprises a DNA coding for a betacellulin protein or a mutein thereof;

(19) A composition for promoting differentiation of undifferentiated pancreatic stem cells to pancreatic beta cells, which comprises a DNA coding for a betacellulin protein or a mutein thereof;

(20) A composition for preventing or treating undifferentiated pancreatic cancer, which comprises a DNA coding for a betacellulin protein or a mutein thereof;

(21) A method for improving pancreatic function of human or mammal, which comprises administering an effective amount of a betacellulin protein or a mutein thereof to human or mammal;

(22) A method for promoting differentiation of undifferentiated pancreatic stem cells to pancreatic beta cells of human or mammal, which comprises administering an effective amount of a betacellulin protein or a mutein thereof to human or mammal;

(23) A method for preventing or treating undifferentiated pancreatic cancer;

(24) A use of a DNA coding for a betacellulin protein or a mutein thereof for the manufacture of a composition for improving pancreatic function;

(25) A use of a DNA coding for a betacellulin protein or a mutein thereof for the manufacture of a composition for promoting differentiation of undifferentiated pancreatic stem cells to pancreatic beta cells; and

(26) A use of a DNA coding for a betacellulin protein or a mutein thereof for the manufacture of a composition for preventing or treating undifferentiated type of pancreatic cancer.

Figure 1:
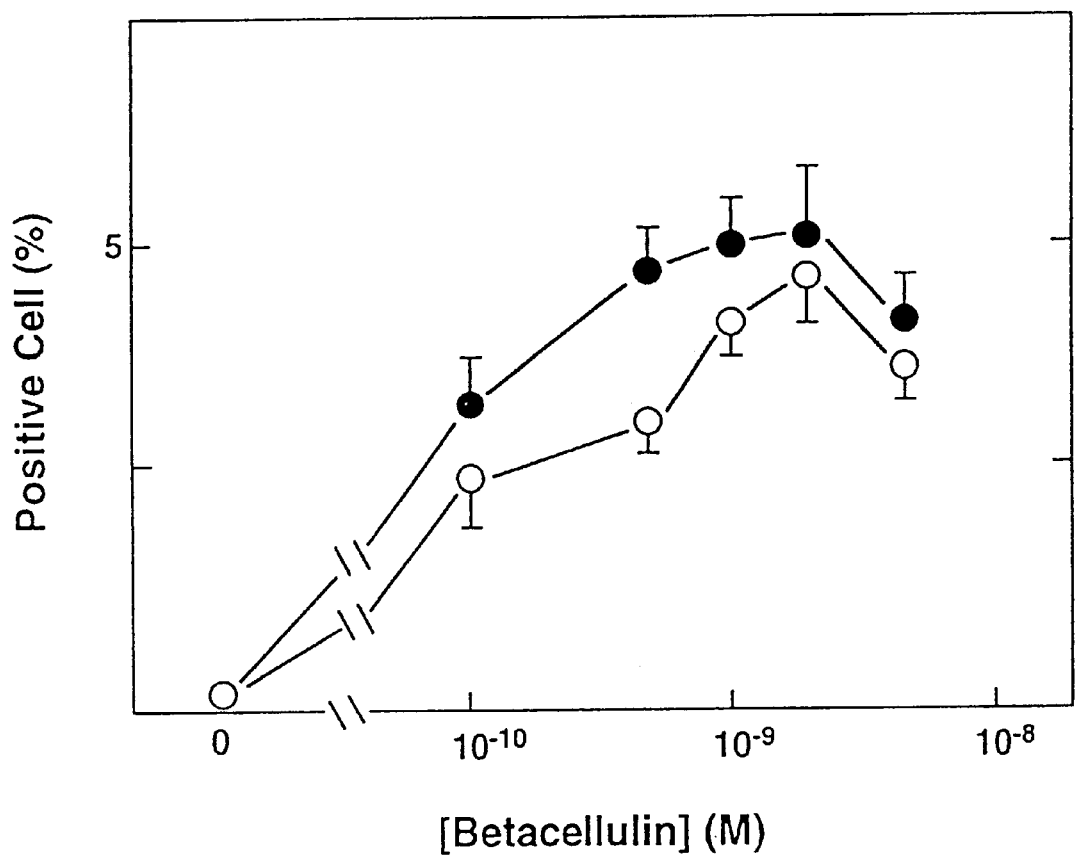
FIG. 1 shows betacellulin protein concentration dependency of differentiation to insulin-producing beta cells or differentiation to pancreatic polypeptide (PP)-producing F cells. The abscissa indicates betacellulin protein concentration (M) and the ordinate indicates the ratio (%) of hormone-producing cells to the total cells. ○ indicates the number of insulin-producing beta cells and ● indicates the number of PP-producing cells.

As BTC protein which can be used for the composition for improving pancreatic function (hereinafter also referred to as composition for improving), the composition for promoting differentiation of undifferentiated pancreatic stem cells to pancreatic beta cells (hereinafter also referred to as composition for promoting) or the composition for preventing or treating undifferentiated type of pancreatic cancer (hereinafter also referred to as composition for preventing or treating undifferentiated type of pancreatic cancer) of the present invention, which comprise BTC protein or a mutein thereof as long as it has BTC-like activity, i.e., growth-promoting activity on fibroblasts, vascular smooth muscle cells, retinal pigment epithelial cells and other cells, any BTC protein can be used. And, non-protein substances, e.g., fermentation products, synthetic compounds and synthetic peptides, can also be used. The BTC protein may be of natural origin, or may be a recombinant protein produced by a gene engineering technique.

As BTC protein of natural origin BTC protein, may be derived from any animal, such as humans, monkeys, hamadryad baboons, chimpanzees, pigs, bovines, sheep, horses, mice and rats. Preferable BTC proteins include those of human or mouse origin, those of human origin are more preferable. It is also preferable to use a BTC protein derived from the same animal species as the animal subject to which the composition for improving, the composition for promoting or the composition for preventing or treating of the present invention is applied. When the composition for improving and so on of the present invention is applied to humans, it is preferable to use BTC protein of human origin.

Examples of BTC proteins are a protein having an amino acid sequence shown by at least one SEQ ID NO. selected from the group consisting of SEQ ID NO. 3, SEQ ID NO. 4, SEQ ID NO. 5 and SEQ ID NO. 6, and so on.

Preferable examples of BTC proteins of human origin are a protein having the amino acid sequence shown by SEQ ID NO:1 (EP-A-0555785) and so on. Examples of BTC proteins of mouse origin are a protein having the amino acid sequence shown by SEQ ID NO:2 [Shing et al., Science, 259:1604 (1993)] and so on.

These BTC proteins may be simple proteins configured with amino acids only, or complex proteins such as glycoproteins, lipoproteins, heme proteins, metal proteins, flavin proteins and phosphoproteins. When the BTC protein is a glycoprotein, examples of its sugar chains are neutral sugars such as D-mannose, D-galactose and L-fructose, amino sugars such as D-glucosamine and D-galactosamine, and sialic acid.

Examples of muteins of BTC protein are deletion-type muteins resulting from deletion of at least one constituent amino acids of the above-described BTC protein, replacement-type muteins resulting from replacement of at least one constituent amino acid of the BTC protein by other amino acids, and addition-type muteins resulting from addition of at least one amino acids to the BTC protein. The number of amino acid deletions, replacements or additions may be any one, as long as the ETC protein retains its essential activity.

Preferable examples of muteins of ETC protein are proteins having (i) an amino acid sequence resulting from deletion of about 1 to 40 amino acids from the amino acid sequence represented by SEQ ID NO:1 or SEQ ID NO:2, (ii) an amino acid sequence resulting from replacement of about 1 to 40 amino acids in the amino acid sequence represented by SEQ ID NO:1 or SEQ ID NO:2 by other amino acid sequences, or (iii) an amino acid sequence resulting from addition of about 1 to 40 amino acids to the amino acid sequence represented by SEQ ID NO:1 or SEQ ID NO:2, and more preferable examples of muteins of BTC protein are proteins having at least one of the following partial amino acid sequences:

1) His Phe Ser Arg Cys Pro Lys Gln Tyr Lys His Tyr Cys Ile (SEQ ID NO:3),
2) Gly Arg Cys Arg Phe Val Val (SEQ ID NO:4),
3) Glu Gln Thr Pro Ser Cys (SEQ ID NO:5), and
4) Gly Ala Arg Cys Glu Arg Val Asp Leu Phe Tyr (SEQ ID NO:6).

Of these muteins, deletion-type muteins etc. are preferred, and proteins having an amino acid sequence resulting from deletion of about 1 to 40 amino acids from the N-terminus of the amino acid sequence represented by SEQ ID NO:1 or SEQ ID NO:2 are more preferable. More specifically, preferable examples of deletion-type muteins of BTC protein are deletion-type muteins of human or mouse BTC protein having an amino acid sequence resulting from deletion of 12 or 30 amino acids from the N-terminus of the amino acid sequence represented by SEQ ID NO:1 or SEQ ID NO:2 [Watanabe et al., Journal of Biochemistry, 269:9966 (1994)]. More preferable examples of deletion-type muteins are deletion-type muteins of human BTC protein having an amino acid sequence resulting from 12 or 30 amino acids from the N-terminus of the amino acid sequence represented by SEQ ID NO:1.

As any other BTC protein mutein, as long as the activity of the BTC protein is retained, any proteins such as muteins resulting from acylation of the N-terminus of BTC protein, those resulting from glycosylation, and those resulting from chemical modification such as polyethylene glycol derivatives are used.

Of the BTC proteins or muteins thereof used for the composition for improving, the composition for promoting or the composition for preventing or treating undifferentiated type of pancreatic cancer of the present invention, the human BTC protein having the amino acid sequence represented by SEQ ID NO:1, deletion-type human BTC muteins having an amino acid sequence resulting from deletion of 12 or 30 amino acids from the N-terminus of the amino acid sequence represented by SEQ ID NO:1, and mouse BTC proteins having the amino acid sequence represented by SEQ ID NO:2 are known; and the other BTC proteins and muteins thereof can be produced by known methods or modifications based thereon.

Also, the C-terminal carboxyl group of the BTC proteins or muteins thereof can be an amide ($-CONH_2$) or an ester thereof.

The salt of said BTC protein or a mutein thereof of the present invention includes preferably pharmaceutically acceptable acid addition salts. Examples of such salts are salts thereof with inorganic acids(e.g. hydrochloric acid, phosphoric acid, hydrobromic acid, sulfuric acid, etc.), salts thereof with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.), etc.

BTC proteins may be manufactured by synthesizing methods for peptides which are known per se by those skilled in the art or methods similar thereto or by cleaving (digesting) BTC protein of the present invention or a precursor thereof by a suitable peptidase. Methods of synthesizing peptide may be any of a solid phase synthesis and a liquid phase synthesis. Thus, a partial peptide or amino acids which can construct the protein of the present invention or a precursor thereof is condensed with the residual part thereof and, when the product has a protective group, said protective group is detached whereupon a desired peptide can be manufactured. Examples of the known methods for condensation and for detachment of protective groups include the following ① to ⑤:

① M. Bodanszky and M. A. Ondetti: Peptide Synthesis, Interscience Publishers, New York (1966).
② Schroeder and Luebke: The Peptide, Academic Press, New York, 1965.
③ Nobuo Izumiya et al.: Fundamentals and Experiments of the Peptide Synthesis, Maruzen KK, Japan (1975).
④ Haruaki Yajima and Shumpei Sakakibara: "Seikagaku Jikken Koza 1" (Experiments of Biochemistry, Part 1), "Tanpakusitu No Kagaku IV" (Chemistry of Protein, IV), p.205 (1977), Japan.
⑤ Haruaki Yajima (ed): Development of Pharmaceuticals (Second Series), Vol. 14, Peptide Synthesis, Hirokawa Shoten, Japan.

After the reaction, conventional purifying techniques such as salting-out, extraction with solvents, distillation, column chromatography, liquid chromatography, electrophoresis, recrystallization, etc. are optionally combined so that the protein of the present invention or a precursor thereof can be purified and isolated. When the protein obtained as such is a free compound, it may be converted to a suitable salt by known methods while, when it is obtained as a salt, the salt may be converted to a free compound or other salt compounds by known methods.

In addition to the above-described BTC protein or a mutein thereof, the composition for improving, the composition for promoting and the composition for preventing or treating undifferentiated type of pancreatic cancer of the present invention may comprise activin.

Activin is known as a hormone that promotes follicle-stimulating hormone secretion (Jikken Igaku, Vol. 10, No. 15, 1992). Examples of activin are activin A, activin B and activin AB, and preferable examples are activin A and so on. These activins may be commercial products (Austral Biological).

Because activin enhances BTC protein's activity, though it does not have BTC protein's activity, it is preferable to use it with BTC protein.

Also, activin is preferably used as formulated in the composition for improving and so on of the present invention. However it may be prepared separately from BTC protein to enable combined use of a composition comprising the BTC protein and a composition comprising activin in order to enhance BTC protein action.

As a DNA coding for BTC protein or a mutein thereof which can be used for the composition for improving pancreatic function (hereinafter also referred to as DNA-containing composition for improving), the composition for promoting differentiation of undifferentiated pancreatic stem cells to pancreatic beta cells (hereinafter also referred to as DNA-containing composition for promoting) or composition for preventing or treating undifferentiated type of pancreatic cancer (hereinafter also referred to as DNA-containg composition for preventing or treating undifferentiated type of pancreatic cancer) of the present invention, which comprise a DNA coding for BTC protein or a mutein thereof, any DNAs coding for the above mentioned BTC protein or a mutein thereof can be used.

The DNAs may be any one of a genome DNA, a genome DNA library, a tissue and cell-derived cDNA, a tissue and cell-derived CDNA library and a synthetic DNA. The vector used for the library may include bacteriophage, plasmid, cosmid, phagemid, etc. The DNA can be further amplified directly by the reverse transcriptase polymerase chain reaction (hereinafter briefly referred to as "RT-PCR" using mRNA fractions prepared from tissues and cells.

Examples of DNAs coding for the human BTC protein represented by SEQ ID NO. 1 are, for example, a DNA comprising a nucleotide sequence represented by SEQ ID NO. 7 (EP-A-0555785) and so on. Examples of DNAs coding for the mouse BTC protein represented by SEQ ID NO. 2 are, for example, a DNA comprising a nucleotide sequence represented by SEQ ID NO. 8 (Science, 259: 1604 (1993)) and so on.

The DNA coding for the BTC protein or a mutein thereof can be cloned by (1) carrying out the PCR amplification using a synthetic DNA primer having a partial nucleotide sequence of the DNA coding for the BTC protein or a mutein thereof; or (2) effecting the selection of a DNA constructed in a suitable vector, based on the hybridization with a labeled DNA fragment or a labeled synthetic DNA coding for a part or all of the BTC protein or a mutein thereof. The hybridization is carried out according to methods as disclosed in, for example, Molecular Cloning, 2nd Ed., J. Sambrook et al., Cold Spring Harbor Lab. Press, 1989. When a DNA library commercially available in the market is used, the hybridization is carried out according to protocols manuals attached thereto. Specifically, the DNA coding for the BTC protein or a mutein thereof can be cloned according to the method as described in EP-A-0482623, EP-A-0555785, Science, 259:1604 (1993) and so on, or the methods similar thereto.

The cloned BTC protein or a mutein thereof can be used as it is, or can be used, as desired, after modifications such as digestion with a restriction enzyme or addition of a linker or adapter, etc., depending upon objects. The DNA may have an initiation codon, ATG, on the 5' terminal side and a termination codon, TAA, TGA or TAG, on the 3' terminal side. These initiation and termination codons can be ligated by using a suitable synthetic DNA adapter.

An expression vector for the BTC protein or a mutein thereof can be produced by, for example, (a) cutting out a target DNA fragment from the DNA coding for the BTC protein or a mutein thereof and (b) ligating the target DNA fragment with the downstream site of a promoter in a suitable expression vector. Specifically, the expression vector for the BTC protein or a mutein thereof can be produced according to the method as described in EP-A-0482623, EP-A-0555785, Science, 259:1604 (1993) and so on, or the methods similar thereto.

The composition for improving, the composition for promoting or the composition for preventing or treating undifferentiated type of pancreatic cancer of the present invention can be produced in accordance with known methods of pharmaceutical making, using pharmaceutically acceptable carriers (including diluents and excipients) as desired.

For example, an aqueous solution for injection of the improving agent of the present invention can be produced by ordinary means using solvents such as water (e.g., distilled water), aqueous solvents (e.g., physiological saline, Ringer's solution) and oily solvents (e.g., sesame oil, olive oil), as desired with additives such as dissolution aids (e.g., sodium salicylate, sodium acetate), buffers (e.g., glucose, invert sugar), stabilizers (e.g., human serum albumin, polyethylene glycol), preservatives (e.g., benzyl alcohol, phenol), and soothing agents (e.g., benzalkonium chloride, procaine hydrochloride).

The said aqueous solution for injection is adjusted to pH about 3 to 8, preferably pH about 5 to 7. To adjust liquid nature within the above pH range, dilute hydrochloric acid, dilute alkali (e.g., dilute sodium hydroxide, dilute sodium hydrogen carbonate) etc. may be added.

The BTC protein content in the composition for improving, the composition for promoting or the composition for preventing or treating of the present invention is normally about 1 to 95% by weight, preferably about 10 to 80% by weight, and more preferably about 20 to 70% by weight, relative to the entire preparation.

The activin content in the composition for improving, the composition for promoting or the composition for preventing or treating of the present invention is normally about 0 to 90% by weight, preferably about 0 to 80% by weight, relative to the entire preparation.

The content ratio of BTC protein and activin is normally about 1:10 to 10:1, preferably about 1:5 to 5:1, and more preferably about 1:2 to 2:1, with preference given to ratios of about 1:2.

The contents of other components (carrier etc.) can be chosen as appropriate, as long as the activity of BTC protein is not inhibited. They are normally about 0.01 to 90% by weight, preferably about 0.1 to 80% by weight, relative to the entire preparation.

In making the composition of the present invention, it is advantageous to further add human serum albumin (HSA) to the aqueous solution containing BTC protein to adjust its liquid nature to pH about 3 to 8, since BTC protein activity reduction during storage is suppressed.

Any HSA type can be used, and preferable examples of HSA are those having a quality for parenteral administration for clinical application of the composition of the present invention. For example, HSA prepared by fractionally purifying plasma from a healthy human by Cohn's method 6 of ethanol fractionation can be used. Also, acetyltryptophan sodium or sodium caprylate may be contained as a stabilizer. When prepared as an aqueous solution, HSA is preferably contained at about 0.1 to 50 mg, particularly 0.5 to 20 mg, per ml of aqueous solution.

In addition to the above-described HSA, the composition for improving, the composition for promoting or the composition for preventing or treating of the present invention of the present invention may contain 1 or more substances selected from the group consisting of amino acids such as glycine, glutamic acid, aspartic acid, alanine and proline, monoamino aliphatic amino acids and cyclic amino acids, monosaccharides such as glucose and mannose, sugar alcohols such as sorbitol and mannitol, and physiologically acceptable salts or derivatives thereof. When the composition prepared as an aqueous solution, the composition preferably contains about 10 to 100 mg of monosaccharides or sugar alcohols and about 5 to 50 mg of amino acids per ml of aqueous solution.

When an acidic amino acid such as glutamic acid is added to adjust the solution nature of the preparation of the composition of the present invention, which contains HSA to pH about 5 to 7, the desired liquid nature can be achieved by adding said substance at the above-specified amount. When no acidic amino acids are added as desired, mineral acids such as hydrochloric acid and phosphoric acid, or buffers such as succinic acid, tartaric acid and citric acid, are used to achieve the desired liquid nature.

As the composition for improving of the present invention is of low toxicity, it can be used as a safe composition for improving pancreatic function against pancreatic dysfunction and hypofunction. Specifically, the composition for improving of the present invention has an activity for promoting pancreatic beta cell differentiation as a cell differentiation promoting factor. In other words, the composition for improving of the present invention is capable of acting on undifferentiated pancreatic stem cells to allow them to differentiate to pancreatic beta cells. The pancreatic beta cells thus produced via such inductive differentiation can secrete and produce insulin.

The composition for improving of the present invention also has an activity for induce differentiation of undifferentiated pancreatic stem cells to other pancreatic cells such as F cells which produce pancreatic peptides (hereinafter also referred to as PP). And, the composition for improving of the present invention has a glucose tolerance-improving activity in vivo. Therefore, the composition for improving of the present invention is therefore useful as a composition (prophylactic/therapeutic agent) improving for diabetes mellitus (e.g., insulin-dependent diabetes mellitus), pancreatic dysfunction in diabetes mellitus, pancreatic hypofunction associated with senile insulin secretion reduction etc.

Also, the composition for promoting of the present invention can also be used as a safe composition for promoting differentiation of undifferentiated pancreatic stem cells to pancreatic beta cells, a composition for promoting an insulin secretion and so on.

As the composition for preventing or treating undifferentiated type of pancreatic cancer is of low toxicity, it can be used as a safe composition for preventing or treating undifferentiated type of pancreatic cancer.

Examples of subject animals of the composition of the present invention are human or mammals such as monkeys, hamadryad baboons, chimpanzees, pigs, bovines, sheep, horses, mice and rats.

The method of administration may be oral and or non-oral, non-oral administration is preferred. For example, non-oral administration can be achieved by intravenous injection or subcutaneous injection.

Specific dose levels of the composition for improving or the composition for promoting may vary depending on subject animal, severity of pancreatic dysfunction and other factors, the amount of the composition of the present invention used is normally about 0.02 $\mu$g to 10 mg/kg, preferably about 2 $\mu$g to 2 mg/kg, as a daily dose of BTC protein, for an adult, when used as an injectable preparation.

Specific dose of the composition for preventing or treating undifferentiated type of pancreatic cancer may vary depending on subject animal, severity of undifferentiated type of pancreatic cancer, the amount of the composition of the present invention used is normally about 0.02 $\mu$g to 10 mg/kg, preferably about 2 $\mu$g to 2 mg/kg, as a daily dose of BTC protein, for an adult, when used as an injectable preparation.

The DNA-containing composition for improving, the DNA-containing composition for promoting or the DNA-containing composition for preventing or treating undifferentiated type of pancreatic cancer of the present invention can be prepared by the same method as the above mentioned method for preparing the composition which comprises BTC protein or a mutein thereof, said DNA alone or a suitable vector such as retrovirus vector, adenovirus vector, adenovirus-associated virus vector wherein said DNA is inserted.

As the DNA-containing composition for improving of the present invention is of low toxicity, it can be used as a safe composition for improving pancreatic function against pancreatic dysfunction and hypofunction. Specifically, the DNA-containing composition for improving of the present invention has an activity for promoting pancreatic beta cell differentiation as a cell differentiation promoting factor. In other words, the DNA-containing composition for improving of the present invention is capable of acting on undifferentiated pancreatic stem cells to allow them to differentiate to pancreatic beta cells. The pancreatic beta cells thus produced via such inductive differentiation can secrete and produce insulin. The DNA-containing composition for improving of the present invention also has an activity for induce differentiation of undifferentiated pancreatic stem cells to other pancreatic cells such as F cells which produce PP. And, the composition for improving of the present invention has a glucose tolerance-improving activity in vivo.

The DNA-containing composition for proving of the present invention is therefore useful as a composition (prophylactic/therapeutic agent) improving for diabetes mellitus (e.g., insulin-dependent diabetes mellitus) pancreatic dysfunction in diabetes mellitus, pancreatic hypofunction associated with senile insulin secretion reduction etc.

Also, the DNA-containing composition for promoting of the present invention can also be used as a safe composition for promoting differentiation of undifferentiated pancreatic stem cells to pancreatic beta cells, a composition for promoting an insulin secretion and so on.

As the DNA-containing composition for preventing or treating undifferentiated type of pancreatic cancer is of low toxicity, it can be used as a safe composition for prevening or treating undifferentiated type of pancreatic cancer.

Examples of subject animals of the DNA-containing composition of the present invention are human or mammals such as monkeys, hamadryad baboons, chimpanzees, pigs, bovines, sheep, horses, mice and rats.

The method of administration may be oral or non-oral, non-oral administration is preferred. For example, non-oral administration can be achieved by intravenous injection or subcutaneous injection.

Specific dose levels of the DNA-containing composition for improving, the DNA-containing composition for promoting or the DNA-containing composition for preventing or treating undifferentiated type of pancreatic cancer of the present invention may vary depending upon a variety of factors including the object to be administered, the age, body weight, general health, sex, diet, time of administration, route of administration, and the severity of the symptom. In the case of oral administration, it is usually about 0.1 to 100 mg, preferably about 1.0 to 50 mg or, more preferably, about 1.0 to 20 mg per day for adults (as 60 kg). When it is administered parenterally, its dose at a time may vary depending upon the object to be administered, organs to be administered, symptoms, administering methods, etc. but, in the case of injections, it is usually convenient to give by an intravenous route in an amount of about 0.01 to 30 mg, preferably about 0.1 to 20 mg or, more preferably, about 0.1 to 10 mg per day to adults (as 60 kg). In the case of other animals, the dose calculated for 60 kg may be administered as well.

The composition for improving of the present invention, which comprises BTC protein, acts on undifferentiated pancreatic stem cells to promote their differentiation to insulin-producing pancreatic beta cells. It also has an activity for induction of differentiation of undifferentiated stem cells to other pancreatic cells such as F cells which produce pancreatic peptide-producing peptide. The composition for improving of the present invention is useful as a composition for preventing or treating diabetes mellitus (e.g., insulin-dependent diabetes mellitus), pancreatic dysfunction in diabetes mellitus etc. And, the composition for improving is also useful as a composition for preventing or treating undifferentiated type of pancreatic cancer.

EXAMPLES

The present invention is hereinafter described in more detail by means of the following examples and test examples, but the scope of the invention is not limited thereby.

Example 1
Injectable Preparation Containing Human BTC Protein 2.5 g of human BTC protein (SEQ ID NO. 1) was dissolved in 1 liter of distilled water and 1.1 g of human serum albumin (HSA) was added to and dissolved in the resulting solution. The solution was subjected to sterilizing filtration and dispensed 4 ml to each ampules (5 ml volume). After drying in a freeze drying machine, each ampule was sealed to yield an ampule for dissolution before use. To use the ampule, it is opened and the contents are dissolved in 2 ml of physiological saline to yield an injectable solution for subcutaneous, intravenous or intramuscular administration. This injectable preparation is used as a composition for improving, a composition for promoting or a composition for preventing or treating undifferentiated type of pancreatic cancer.

Example 2

Injectable Preparation Containing Human BTC Protein and Activin A 2.5 g of human BTC protein (SEQ ID NO. 1) and 12.5 g of activin A were dissolved in 1 liter of distilled water and 1.0 g of human serum albumin (HSA) was added to and dissolved in the resulting solution. The solution was subjected to sterilizing filtration and dispensed 4 ml to each ampules (5 ml volume). After drying in a freeze drying machine, each ampule was sealed to yield an ampule for dissolution before use. To use the ampule, it is opened and the contents are dissolved in 2 ml of physiological saline to yield an injectable solution for subcutaneous, intravenous or intramuscular administration. This injectable preparation is used as a composition for improving, a composition for promoting or a composition for preventing or treating undifferentiated type of pancreatic cancer.

Example 3
Injectable Preparation Containing DNA Coding for Human BTC Protein 2.5 g of human BTC protein (SEQ ID NO. 1) was dissolved in 1 liter of distilled water and 1.1 g of human serum albumin (HSA) was added to and dissolved in the resulting solution. The solution was subjected to sterilizing filtration and dispensed 4 ml to each ampules (5 ml volume). After drying in a freeze drying machine, each ampule was sealed to yield an ampule for dissolution before use. To use the ampule, it is opened and the contents are dissolved in 2 ml of physiological saline to yield an injectable solution for subcutaneous, intravenous or intramuscular administration. This injectable preparation is used as a DNA composition for improving, a DNA composition for promoting or a DNA composition for preventing or treating undifferentiated type of pancreatic cancer.

Example 4
Injectable Preparation Containing Human BTC Protein 0.5 g of human BTC protein (SEQ ID NO. 1) was dissolved in 1 liter of distilled water and 2.0 g of human serum albumin (HSA) was added to and dissolved in the resulting solution. The solution was subjected to sterilizing filtration and dispensed 4 ml to each ampules (5 ml volume). After drying in a freeze drying machine, each ampule was sealed to yield an ampule for dissolution before use. To use the ampule, it is opened and the contents are dissolved in 2 ml of physiological saline to yield an injectable solution for subcutaneous, intravenous or intramuscular administration. This injectable preparation is used as a composition for improving, a composition for promoting or a composition for preventing or treating undifferentiated type of pancreatic cancer.

Example 5
Injectable Preparation Containing Human BTC Protein and Activin A 2.5 g of human BTC protein (SEQ ID NO. 1) and 5.0 g of activin A were dissolved in 1 liter of distilled water and 1.0 g of human serum albumin (HSA) was added to and dissolved in the resulting solution. The solution was subjected to sterilizing filtration and dispensed 4 ml to each ampules (5 ml volume). After drying in a freeze drying machine, each ampule was sealed to yield an ampule for dissolution before use. To use the ampule, it is opened and the contents are dissolved in 2 ml of physiological saline to yield an injectable solution for subcutaneous, intravenous or intramuscular administration. This injectable preparation is used as a composition for improving, a composition for promoting or a composition for preventing or treating undifferentiated type of pancreatic cancer.

Test Example 1
Effect of BTC Protein on Differentiation to Insulin-producing Beta Cells and Differentiation to Pancreatic Polypeptide-producing F Cells The cell line AR42J [Christophe, American Journal of Physiology, 266:G963 (1994)], derived from a pancreatic cancer induced by a chemical carcinogen, was sown over a glass cover slip at a concentration of $10^5$ cells/ml in Dulbecco's modified Eagle MEM (Flow, USA) containing 20 mM Hepes/NaOH (pH 7.4), 5 mM NaHCO$_3$, 10% fetal bovine serum and various concentrations of human BTC protein (SEQ ID NO:1), and was cultured at 37° C. in a carbon dioxide gas incubator (5% carbon dioxide gas, 95% air). Five days later, the cells were fixed with 3% paraformaldehyde and treated with 0.1% Triton X-100 (trade name) for 5 minutes, after which they were incubated with Blocking Ace (Morinaga Milk Industry Co., Ltd., Japan) and a primary antibody (anti-insulin antibody or anti-pancreatic polypeptide antibody) then a secondary antibody (indocarbocyanine-conjugated donkey anti-rabbit IgG antibody or indocarbocyanine-conjugated donkey anti-guinea pig IgG antibody). The cells were then microscopically examined using Axiophoto, produced by Carl Zeiss (NY, USA). As a result, as shown by ○ in FIG. 1, the number of fluorescently dyed cells, i.e., cells which differentiated to insulin-producing beta cells, increased with dependency on BTC protein concentration; in the presence of $2 \times 10^{-9}$ M BTC protein, up to about 4% cells became insulin-producing beta cells. It was also found that about 5% cells differentiate to pancreatic polypeptide (PP)-producing F cells.

Similar results were obtained from mRNA analysis using RT-PCR. Specifically, in the presence of BTC protein, AR42J cells differentiated so that insulin mRNA, PP mRNA, glucokinase mRNA and glucose transporter 2 mRNA were synthesized, but glucagon mRNA was not detected.

Figure 2:
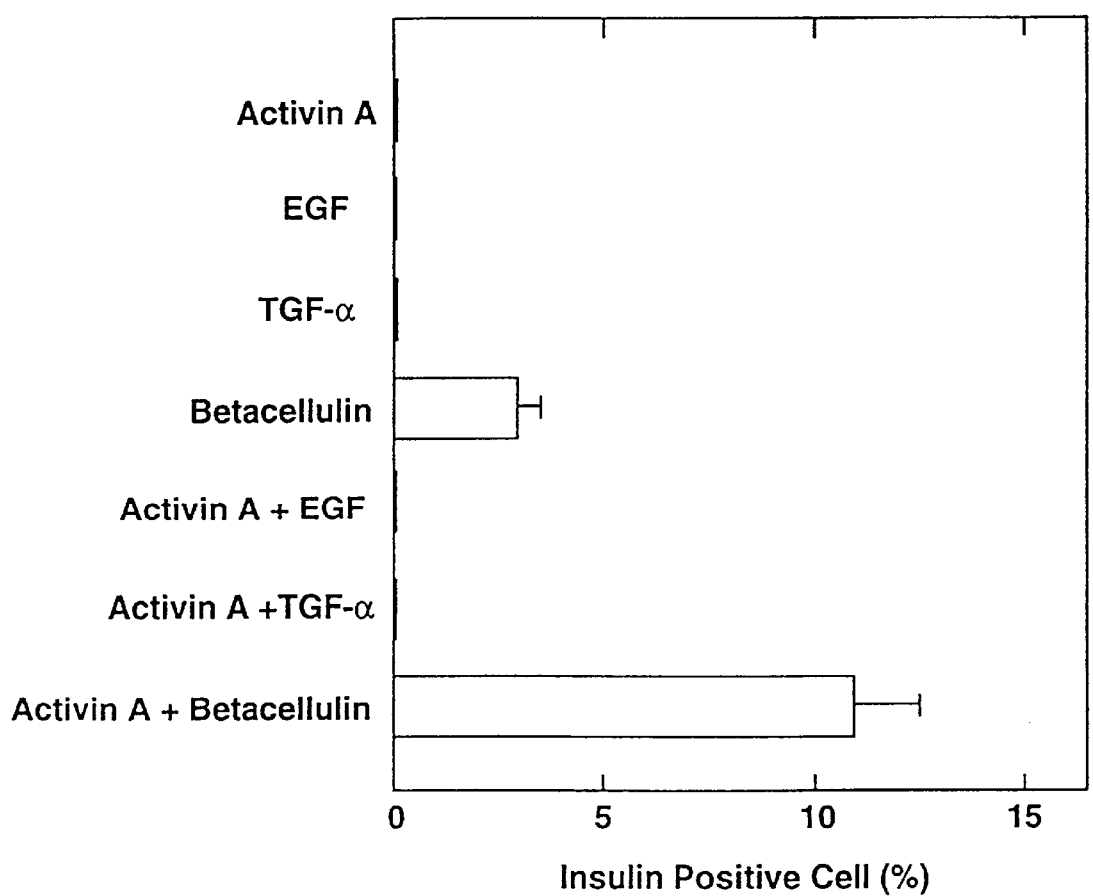
FIG. 2 shows the effects of various factors on differentiation to insulin-producing beta cells. The ordinate indicates factor designations of factors and the abscissa indicates the ratio (%) of insulin-producing cells to the total cells. EGF indicates epithelial growth factor; TGF-α indicates transforming growth factor α; Betacellulin indicates human betacellulin protein. The concentration of Activin A, EGF, TGF-α and betacellulin is $1 \times 10^{-9}$ M, respectively. Activin A+EGF, Activin A+TGF-α and Activin A+Betacellulin indicate the combination of $1 \times 10^{-9}$ M of EGF, TGF-α or betacellulin with $2 \times 10^{-9}$ M of Activin A, respectively.

Test Example 2
Effects of Various Factors on Differentiation to Insulin-producing Beta Cells Using the same conditions as those in Test Example 1, the effects of various factors on differentiation to beta cells were investigated. As seen from some results shown in FIG. 2, $1 \times 10^{-9}$ M epithelial growth factor (EGF), transforming growth factor α (TGF-α), fibroblast growth factor (FGF), insulin-like growth factor (IGF), gastrin, cholecystokinin, TGF-β and activin A all failed to induce differentiation of AR42J cells to insulin-producing beta cells, but $1 \times 10^{-9}$ M human BTC protein (SEQ ID NO. 1) induced differentiation of about 2.5% AR42J cells to insulin-producing beta cells. As shown in FIG. 2, AR42J cells failed to differentiate to insulin-producing beta cells in the presence of $2 \times 10^{-9}$ M activin A and $1 \times 10^{-9}$ M EGF, $2 \times 10^{-9}$ M activin A and $1 \times 10^{-9}$ M TGF-α, but 10% of AR42J cells differentiated to insulin-producing beta cells in the presence of $2 \times 10^{-9}$ M activin A and $1 \times 10^{-9}$ M human BTC protein. The result shows that activin A enhanced the differentiation-inducing activity of BTC protein.

Figure 3:
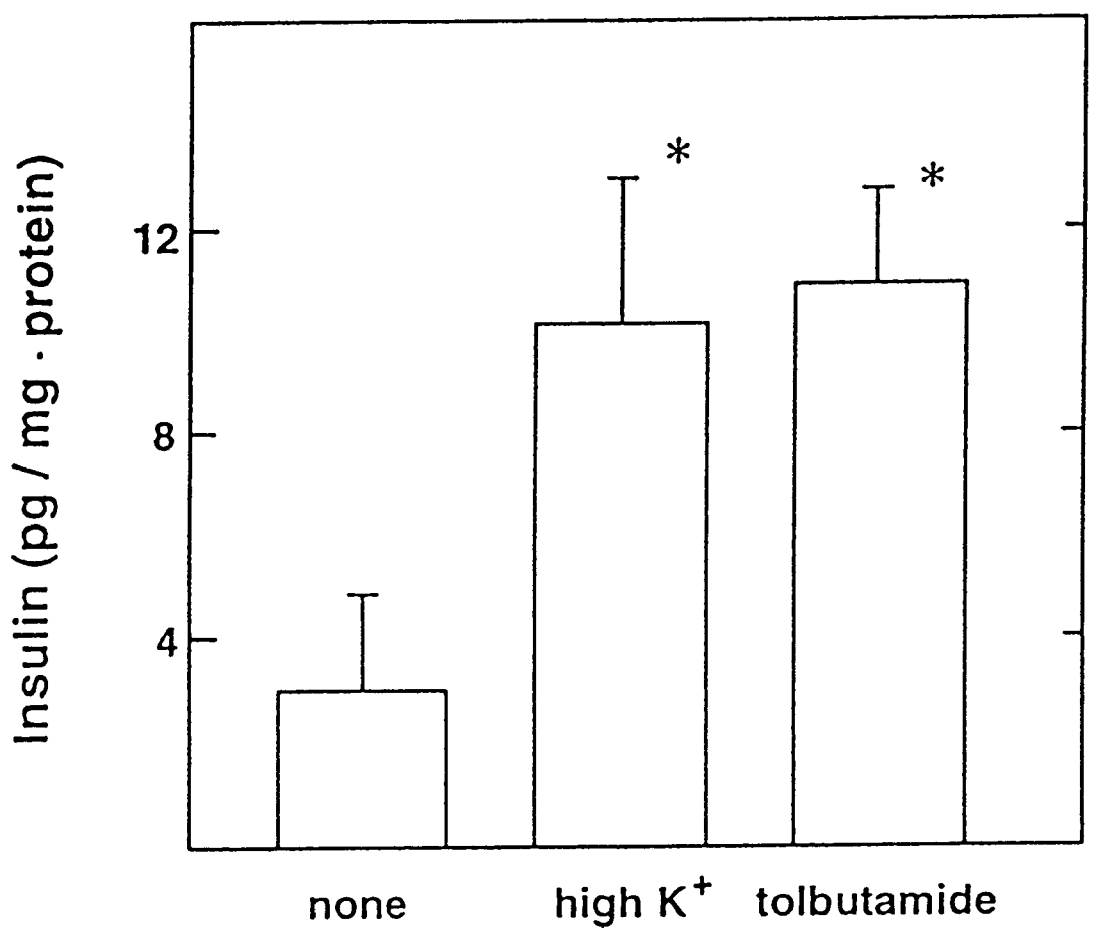
FIG. 3 shows insulin secretion from AR42J cells which have differentiated to insulin-producing beta cells in the presence of potassium ions or tolbutamide. None, high K and tolbutamide on the abscissa indicate the absence of potassium ions and tolbutamide, presence of 40 mM potassium, and 10 $\mu$M tolbutamide, respectively. The ordinate indicates secreted insulin concentration (pg/mg·protein).

Test Example 3
Insulin Secretion in AR42J Cells Which Have Differentiated to Insulin-producing Beta Cells Using the same method as that in Test Example 1, AR42J cells were sown over a dish of 6 cm diameter at a density of $1 \times 10^5$ cells/ml, and were cultured in the presence of $1 \times 10^{-9}$ M human BTC protein (SEQ ID NO. 1) and $2 \times 10^{-9}$ M activin A for 5 days. The cells were then washed with DMEM and incubated for 60 minutes in a Krebs-Ringer bicarbonate buffer containing 5.5 mM glucose in the presence of 10 μM tolbutamide or 40 mM potassium ions. After that the culture broth was collected and assayed for insulin concentration using TR-IFMA (time-resolved immunofluorometric assay system) [Lovgren et al., in "Alternative Immunoassays," ed. by W. P. Collins, John Whiley & Sons Ltd., p. 203 (1985)]. The results shown in FIG. 3 demonstrate that the differentiated AR42J cells secreted significant amounts of insulin in the culture broth, and that this secretion was promoted by high concentrations of potassium ions or tolbutamide.

Test Example 4

Glucose Tolerance-improving Activity of BTC Protein in Diabetic Mice

Figure 4:
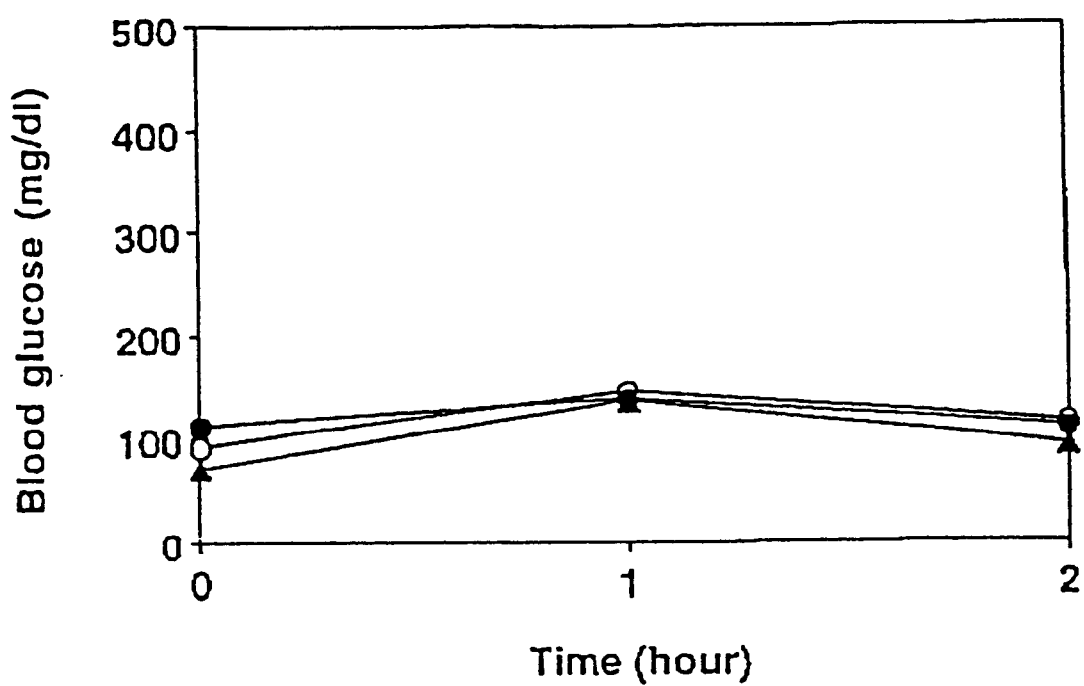
FIG. 4 shows the glucose tolerance-improving activity of human betacellulin protein in diabetic mice in case of intraperitoneal glucose tolerance test (ipGTT) after 0 week before alloxan treatment. The abscissa indicates the time after administering glucose to intraperitoneal. The ordinate indicates blood glucose levels (mg/ml). ○, ● and ▲ show the result of alloxan non-treated mouse, alloxan treated/human betacellulin non-administered mouse and alloxan treated/human betacellulin administered mouse, respectively.
Figure 5:
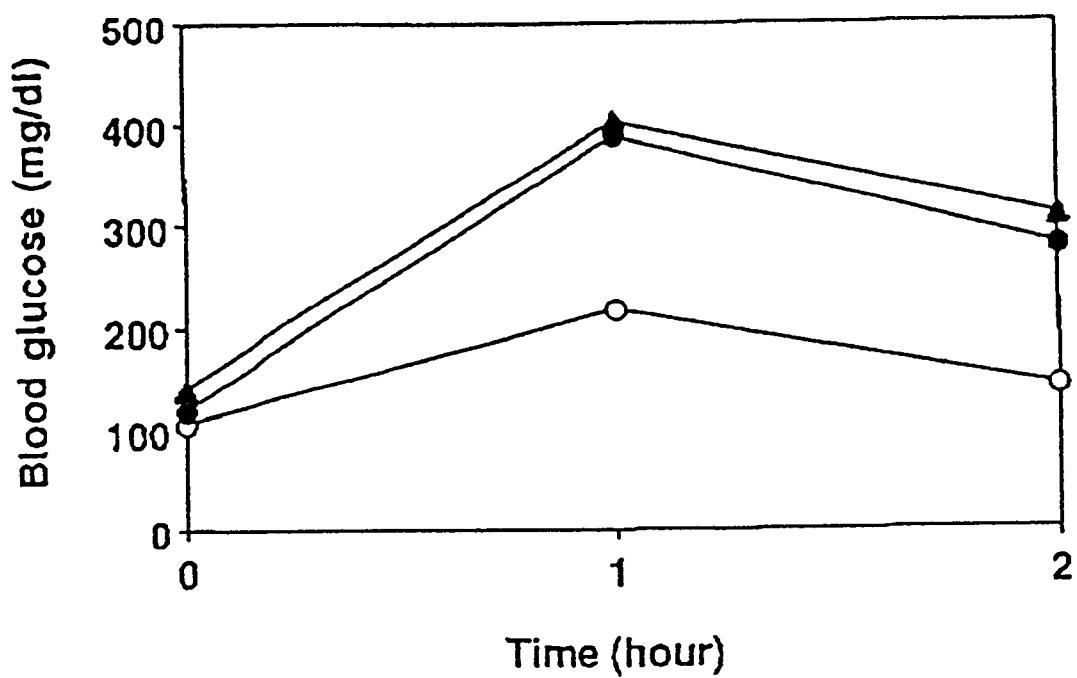
FIG. 5 shows the glucose tolerance-improving activity of human betacellulin protein in diabetic mice in case of intraperitoneal glucose tolerance test (ipGTT) 4 weeks after alloxan treatment. The abscissa indicates the time after administering glucose to intraperitoneal. The ordinate indicates blood glucose levels (mg/ml). ○, ● and ▲ show the result of alloxan non-treated mouse, alloxan treated/human betacellulin non-administered mouse and alloxan treated/human betacellulin administered mouse, respectively.
Figure 6:
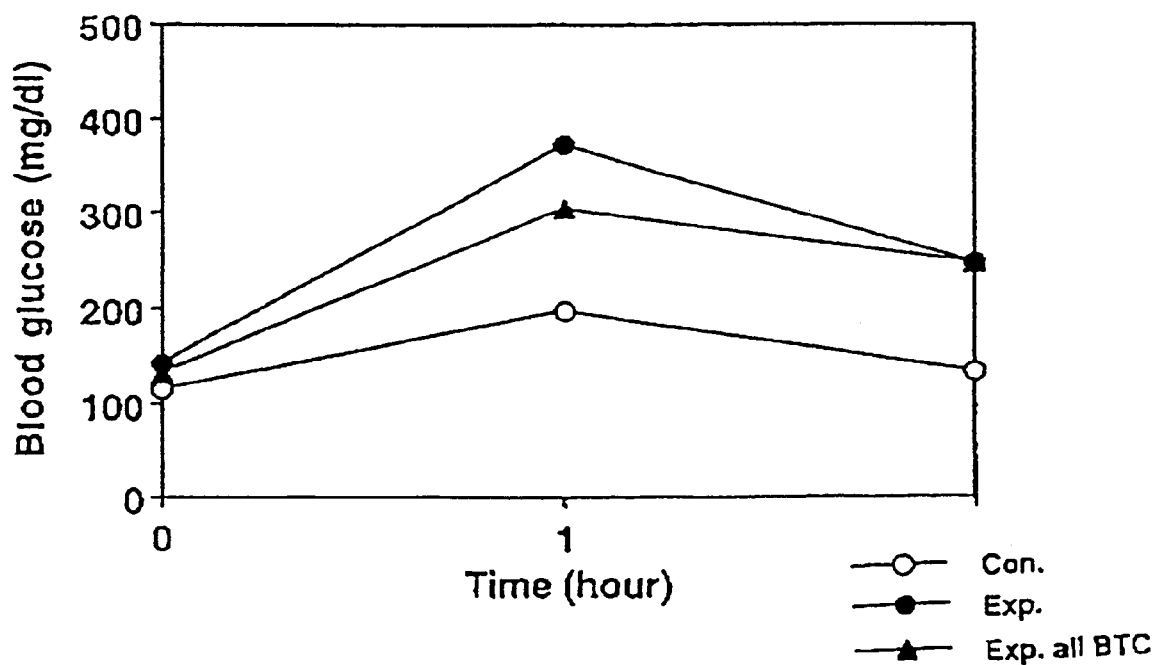
FIG. 6 shows the glucose tolerance-improving activity of human betacellulin protein in diabetic mice in case of intraperitoneal glucose tolerance test (ipGTT) 8 weeks after alloxan treatment. The abscissa indicates the time after administering glucose to intraperitoneal. The ordinate indicates blood glucose levels (mg/ml). ○, ● and ▲ show the result of alloxan non-treated mouse, alloxan treated/human betacellulin non-administered mouse and alloxan treated/human betacellulin administered mouse, respectively.

A male ICR mouse at 8 weeks of age was subjected to partial pancreatic perfusion with alloxan (100 mg/kg body weight; while the superior mesenteric vein was clamped, alloxan was intravenously administered to selectively destroy beta cells in the pancreatic tail and conserve those in the pancreatic head) to yield a diabetic model mouse (Diabetes Frontier, 7:285–286, 1966, and ibid. 7:287–288, 1966). This diabetic mouse was given subcutaneous administration of human BTC protein (SEQ ID NO. 1) at 1 mg/kg body weight/day for 8 consecutive weeks, starting at 1 day after alloxan treatment. Before alloxan treatment and 2, 4 and 8 weeks after alloxan treatment, an intraperitoneal glucose tolerance test (ipGTT) (2 g glucose/kg body weight) was conducted to determine blood glucose levels before glucose loading and 1 and 2 hours after glucose loading, with periodical determination of body weight change. As a result, there was no difference between the BTC protein administration and non-administration groups in case of ipGTT before alloxan treatment (FIG. 4) and 4 weeks after alloxan treatment (FIG. 5). As shown in FIG. 6, however, a markedly decreased blood glucose level was noted 1 hour after glucose loading in the BTC protein administration group (▲) compaired with the BTC protein non-administration group (●) in case of ipGTT 8 weeks after alloxan treatment. The results shown in FIGS. 4 to 6 demonstrate that human BTC protein has a glucose tolerance-improving activity. There was no significant difference in mouse body weight between the administration and non-administration groups.

Test Example 5

Growth-inhibiting Activity of BTC Protein Against Pancreatic Cancer Cells

Figure 7:
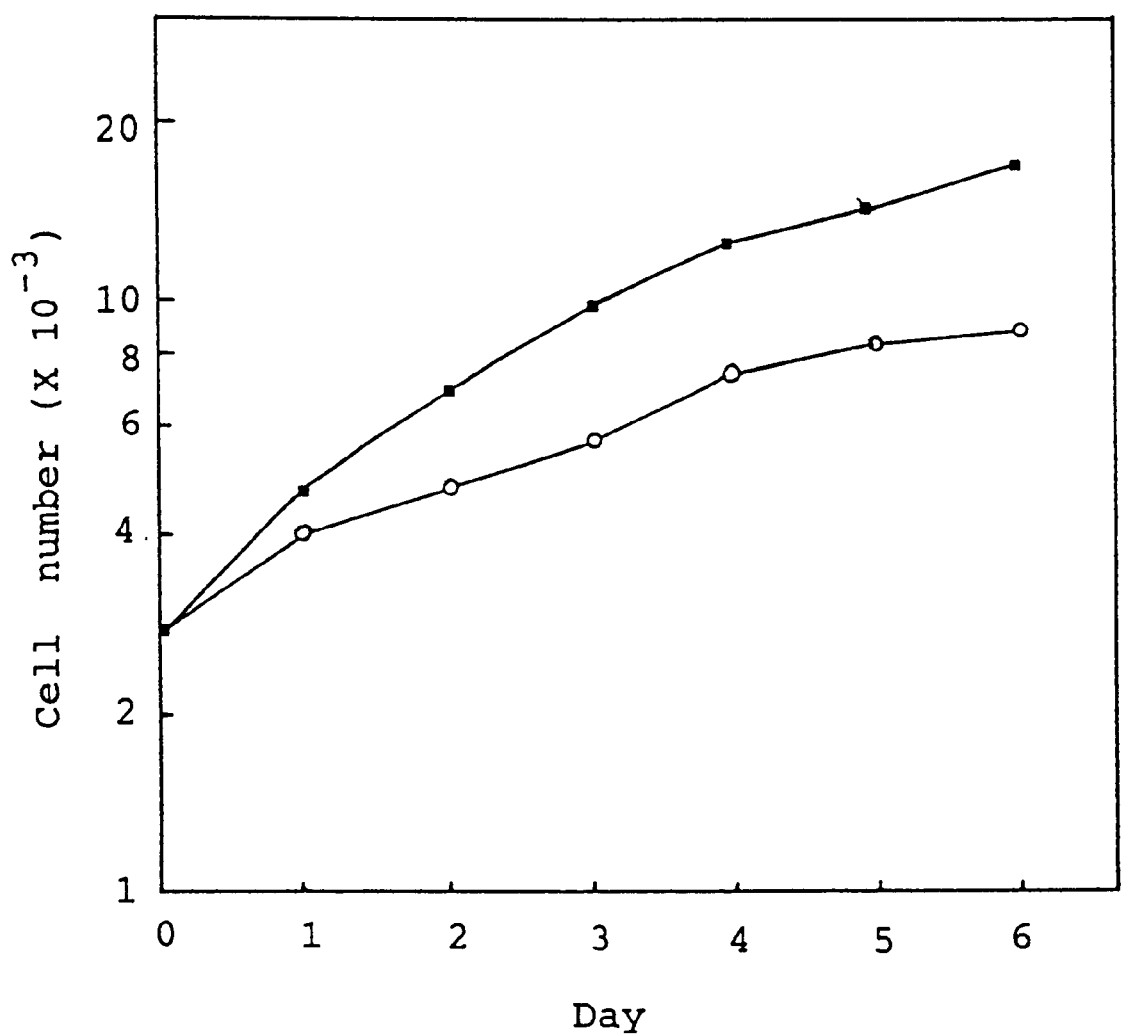
FIG. 7 shows the growth-inhibiting activity of human betacellulin protein against pancreatic cancer cells. The abscissa indicates the culture days. The ordinate indicates the number ($\times 10^{-3}$) of No. 71 clone cells of AR42J cells derived from pancreatic cancer. ○ indicates the result of incubation on human BTC protein-containing medium. ● indicates the result of incubation on non-human BTC protein-containing medium.

About $3 \times 10^3$ of clone 71 cells of AR42J cells were sown over a Falcon-sharle of 3 cm diameter (BectonDickinson, USA) in Dulbecco's modfied Eagle MEM containing 2 nM human BTC protein (SEQ ID NO. 1) and 1% fetal bovine serum, and was cultured at 37° C. in the present of 5% carbon dioxide gas to measure a increase of number of cells periodically by coulter counter. As a control, an increase of number of cells was measured at a condition of absence of human STC protein. The obtained results were shown in FIG. 5. The results shown in FIG. 7 demonstrate that the growth of clone 71 cells in the human BTC protein-containing medium were inhibited clearly compared with that in the non-human STC protein-containing medium.

What is claimed is:

1. A method for treating a mammal comprising administering to said mammal an effective amount of a composition comprising a betacellulin protein wherein said betacellulin protein comprises the amino acid sequence of SEQ ID NO: 1, the amino acid sequence of SEQ ID NO: 2, or a fragment of either of the amino acid sequences of SEQ ID NOs: 1 or 2, and a pharmaceutically acceptable carrier, wherein said betacellulin protein has the activity of
   a) promoting the differentiation of undifferentiated pancreatic cells to insulin-producing beta cells;
   b) promoting the differentiation of undifferentiated pancreatic cells to pancreatic polypeptide producing F cells;
   c) improving glucose tolerance in a patient suffering from below normal insulin activity;
   d) improving glucose tolerance in a patient suffering from insulin-dependent diabetes mellitus; or
   e) inhibiting the growth of undifferentiated pancreatic cancer cells.

2. The method of claim 1, wherein said betacellulin comprises the amino acid sequence of SEQ ID NO: 1 or a fragment of the amino acid sequence of SEQ ID NO: 1.

3. The method of claim 1, wherein said betacellulin comprises the amino acid sequence of SEQ ID NO: 2 or a fragment of the amino acid sequence of SEQ ID NO: 2.

4. The method of claim 1, wherein said mammal is a human.

5. The method of claim 1, wherein the composition further comprises activin.

6. The method of claim 5, wherein the ratio of activin to betacellulin is about 1:10 to 10:1.

7. A method for promoting the differentiation of undifferentiated pancreatic cells to insulin producing beta cells, comprising administering to said undifferentiated pancreatic cells a composition comprising a betacellulin protein, wherein said betacellulin protein comprises the amino acid sequence of SEQ ID NO: 1, the amino acid sequence of SEQ ID NO: 2, or a fragment of either of the amino acid sequences of SEO ID NOs: 1 or 2, and a pharmaceutically acceptable carrier, in an amount which is effective to promote the differentiation of undifferentiated pancreatic cancer cells to insulin producing beta cells.

8. A method for promoting the differentiation of undifferentiated pancreatic cells to pancreatic polypeptide producing F cells, comprising administering to said undifferentiated pancreatic cells a composition comprising a betacellulin protein, wherein said betacellulin protein comprises the amino acid sequence of SEQ ID NO: 1, the amino acid sequence of SEQ ID NO: 2, or a fragment of either of the amino acid sequences of SEQ ID NOs: 1 or 2, and a pharmaceutically acceptable carrier, in an amount which is effective to promote the differentiation of undifferentiated pancreatic cells to pancreatic polypeptide producing F cells.

9. A method for improving glucose tolerance in a patient suffering from below normal insulin activity, comprising administering to said patient a composition comprising a betacellulin protein, wherein said betacellulin protein comprises the amino acid sequence of SEQ ID NO: 1, the amino acid sequence of SEQ ID NO: 2, or a fragment of either of the amino acid sequences of SEQ ID NOs: 1 or 2, and a pharmaceutically acceptable carrier, in an amount which is effective to improve glucose tolerance in said patient.

10. The method of claim 9, wherein said patient is suffering from insulin-dependent diabetes mellitus.

11. A method for inhibiting the growth of pancreatic cancer cells, comprising administering to said pancreatic cancer cells a composition comprising a betacellulin protein, wherein said betacellulin protein comprises the amino acid sequence of SEQ ID NO: 1, the amino acid sequence of SEQ ID NO: 2, or a fragment of either of the amino acid sequences of SEQ ID NOs: 1 or 2, and a pharmaceutically acceptable carrier, in an amount which is effective to inhibit the growth of undifferentiated pancreatic cancer cells.

12. The method of any one of claims 7–9 or 11, wherein the composition further comprises activin.

13. A method for treating a mammal comprising administering to said mammal an effective amount of a composition comprising a betacellulin protein, wherein said betacellulin protein comprises a fragment of either of the amino acid sequences of SEQ ID NOs: 1 or 2 and a pharmaceutically acceptable carrier, wherein said betacellulin protein fragment has the activity of
   a) promoting the differentiation of undifferentiated pancreatic cells to insulin-producing beta cells;
   b) promoting the differentiation of undifferentiated pancreatic cells to pancreatic polypeptide producing F cells;
   c) improving glucose tolerance in a patient suffering from below normal insulin activity;
   d) improving glucose tolerance in a patient suffering from insulin-dependent diabetes mellitus; or
   e) inhibiting the growth of undifferentiated pancreatic cancer cells.

14. The method of claim 13, wherein said betacellulin fragment comprises the amino acid sequence of SEQ ID NO: 3.

15. The method of claim 13, wherein said betacellulin comprises the amino acid sequence of SEQ ID NO: 4.

16. The method of claim 13, wherein said betacellulin fragment comprises the amino acid sequence of SEQ ID NO: 5.

17. The method of claim 13, wherein said betacellulin fragment comprises the amino acid sequence of SEQ ID NO: 6.

18. The method of claim 13, wherein said mammal is a human.

19. The method of claim 13, wherein the composition further comprises activin.

20. The method of claim 19, wherein the ratio of activin to betacellulin fragment is about 1:10 to 10:1.

21. A method for promoting the differentiation of undifferentiated pancreatic cells to insulin producing beta cells, comprising administering to said undifferentiated pancreatic cells a composition comprising a betacellulin protein, wherein said betacellulin protein comprises a fragment of either of the amino acid sequences of SEQ ID NOs: 1 or 2 and a pharmaceutically acceptable carrier, in an amount which is effective to promote the differentiation of undifferentiated pancreatic cancer cells to insulin producing beta cells.

22. A method for promoting the differentiation of undifferentiated pancreatic cells to pancreatic polypeptide producing F, cells comprising administering to said undifferentiated pancreatic cells a composition comprising a betacellulin protein, wherein said betacellulin protein comprises a fragment of either of the amino acid sequences of SEQ ID NOs: 1 or 2 and a pharmaceutically acceptable carrier, in an amount which is effective to promote the differentiation of undifferentiated pancreatic cells to pancreatic polypeptide producing F cells.

23. A method for improving glucose tolerance in a patient suffering from below normal insulin activity, comprising administering to said patient a composition comprising a betacellulin protein, wherein said betacellulin protein comprises a fragment of either of the amino acid sequences of SEQ ID NOs: 1 or 2 and a pharmaceutically acceptable carrier, in an amount which is effective to improve glucose tolerance in said patient.

24. The method of claim 23, wherein said patient is suffering from insulin-dependent diabetes mellitus.

25. A method for inhibiting the growth of pancreatic cancer cells, comprising administering to said pancreatic cancer cells a composition comprising a betacellulin protein, wherein said betacellulin protein comprises a fragment of either of the amino acid sequences of SEQ ID NOs: 1 or 2 and a pharmaceutically acceptable carrier, in an amount which is effective to inhibit the growth of undifferentiated pancreatic cancer cells.

26. The method of any one of claims 21–23 or 25, wherein the composition further comprises activin.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:1:

```
Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Gln Ser Lys Arg Lys
                20                  25                  30

Gly His Phe Ser Arg Cys Pro Lys Gln Tyr Lys His Tyr Cys Ile Lys
                35                  40                  45

Gly Arg Cys Arg Phe Val Val Ala Glu Glu Thr Pro Ser Cys Val Cys
                50                  55                  60

Asp Glu Gly Tyr Ile Gly Ala Arg Cys Glu Arg Val Asp Leu Phe Tyr
65                  70                  75                  80
```

(2) INFORMATION FOR SEQ ID NO:2:

(i) SEQUENCE CHARACTERISTICS:
        (A) LENGTH: 80 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Asp Gly Asn Thr Thr Arg Thr Pro Glu Thr Asn Gly Ser Leu Cys Gly
1               5                   10                  15

Ala Pro Gly Glu Asn Cys Thr Gly Thr Thr Pro Arg Gln Lys Val Lys
                20                  25                  30

Thr His Phe Ser Arg Cys Pro Lys Gln Tyr Lys His Tyr Cys Ile His
                35                  40                  45

Gly Arg Cys Arg Phe Val Val Asp Glu Gln Thr Pro Ser Cys Ile Cys
                50                  55                  60

Glu Lys Gly Tyr Phe Gly Ala Arg Cys Glu Arg Val Asp Leu Phe Tyr
65                  70                  75                  80
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
His Phe Ser Arg Cys Pro Lys Gln Tyr Lys His Tyr Cys Ile
1               5                   10
```

(2) INFORMATION FOR SEQ ID NO:4:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

Gly Arg Cys Arg Phe Val Val
1            5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

Glu Gln Thr Pro Ser Cys
1            5

(2) INFORMATION FOR SEQ ID NO:6:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Gly Ala Arg Cys Glu Arg Val Asp Leu Phe Tyr
1            5                10

(2) INFORMATION FOR SEQ ID NO:7:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:7:

```
GATGGGAATT CCACCAGAAG TCCTGAAACT AATGGCCTCC TCTGTGGAGA CCCTGAGGAA      60

AACTGTGCAG CTACCACCAC ACAATCAAAG CGGAAAGGCC ACTTCTCTAG GTGCCCCAAG     120

CAATACAAGC ATTACTGCAT CAAAGGGAGA TGCCGCTTCG TGGTGGCCGA GCAGACGCCC     180

TCCTGTGTCT GTGATGAAGG CTACATTGGA GCAAGGTGTG AGAGAGTTGA CTTGTTTTAC     240
```

(2) INFORMATION FOR SEQ ID NO:8:

(i) SEQUENCE CHARACTERISTICS:
        (A) LENGTH: 240 base pairs
        (B) TYPE: nucleic acid
        (C) STRANDEDNESS: double
        (D) TOPOLOGY: linear (ii) MOLECULE TYPE: cDNA -continued (xi) SEQUENCE DESCRIPTION: SEQ ID NO:8:

```
GATGGGAACA CAACCAGAAC ACCAGAAACC AATGGCTCTC TTTGTGGAGC TCCTGGGGAA      60

AACTGCACAG GTACCACCCC TAGACAGAAA GTGAAAACCC ACTTCTCTCG GTGCCCCAAG     120

CAGTACAAGC ATTACTGCAT CCATGGGAGA TGCCGCTTCG TGGTGGACGA GCAAACTCCC     180

TCCTGCATCT GTGAGAAAGG CTACTTTGGG GCTCGGTGTG AGCGAGTGGA CCTGTTTTAC     240
```